United States Patent [19]

Duvall et al.

[11] 4,083,950

[45] Apr. 11, 1978

[54] STABLE ACETYLSALICYLIC ACID AND PHENYLPROPANOLAMINE SALT COMPOSITION

[75] Inventors: Ronald Nash Duvall; Gerald Gold, both of Elkhart, Ind.

[73] Assignee: Miles Laboratories, Inc., Elkhart, Ind.

[21] Appl. No.: 664,685

[22] Filed: Mar. 8, 1976

[51] Int. Cl.² .................... A61K 9/00; A61K 31/615
[52] U.S. Cl. .................................. 424/44; 424/233; 424/313; 424/330
[58] Field of Search ............................ 424/233, 44

[56] References Cited

U.S. PATENT DOCUMENTS 2,427,887  9/1947  Wallace ................................ 424/233
3,567,819  3/1971  Idson et al. .......................... 424/16

OTHER PUBLICATIONS

Chemical Abstracts 59:885b (1963).
Registered Trademark 864,883 (2/18/69).
Handbook of Non-Prescription Drugs, 5th ed., 1977, p. 106.
Handbook of Non-Prescription Drugs, 1973, pp. 32-35.

*Primary Examiner*—Leonard Schenkman
*Attorney, Agent, or Firm*—Louis E. Davidson

[57] ABSTRACT

A stable composition containing acetylsalicylic acid and a nasal decongestant is disclosed wherein the decongestant is the bitartrate or tartrate salt of phenylpropanolamine or mixture of such salts.

6 Claims, No Drawings

STABLE ACETYLSALICYLIC ACID AND PHENYLPROPANOLAMINE SALT COMPOSITION

BACKGROUND AND PRIOR ART

Medicinal compositions containing acetylsalicylic acid are well-known. It is also known that when acetylsalicylic acid is used in conjunction with other active ingredients the other ingredients can cause some instability in the acetylsalicylic acid resulting in the undesirable formation of salicylic acid or other reaction products. In order to prevent such instability, it is often necessary to physically separate the acetylsalicylic acid component from the other ingredients. This can be accomplished by using a layered composition, such as a layered tablet or press-coated tablet, or by coating the ingredients with a layer or film of suitable protective material.

When a nasal decongestant, such as phenylephrine hydrochloride, is used in conjunction with acetylsalicylic acid, the resulting combination causes considerable instability of the acetylsalicylic acid and reaction between the ingredients, such as formation of acetyl derivatives of phenylephrine, unless a coated or layered composition is employed. Such techniques can be complex and expensive. When an effervescent composition is desired, such techniques are either not feasible or they adversely affect effervescence or solution characteristics. It was known in the prior art that a stable mixture of acetylsalicylic acid and phenylephrine bitartrate could be employed without the requirements of layering or coating.

Recently it was proposed to replace phenylephrine with phenylpropanolamine as the nasal decongestant in admixture with acetylsalicylic acid. The only readily available salt of phenylpropanolamine was phenylpropanolamine hydrochloride. It is known that primary amines are more reactive than secondary amines. It was therefore reasonable to expect that salts of phenylpropanolamine (a primary amine) would be more reactive with and thus cause more instability of acetylsalicylic acid than salts of phenylephrine (a secondary amine). Phenylpropanolamine salts are also known to be pharmacologically less effective on a weight basis than phenylephrine salts. Therefore it requires more of the phenylpropanolamine salts to achieve the desired medicinal effect. The increased amounts of the more reactive phenylpropanolamine salts should reasonably cause more instability of acetylsalicylic acid that the corresponding salts of phenylephrine. The use of specific salts of phenylpropanolamine in direct contact with acetylsalicylic acid to provide a storage-stable composition is therefore an advance in the art.

SUMMARY OF THE INVENTION

In accordance with the present invention, a stable composition is provided comprising a substantially uniform mixture of acetylsalicylic acid and a bitartrate or tartrate salt of phenylpropanolamine or a mixture of such salts in direct contact with the acetylsalicylic acid. In particular the present invention provides a stable composition that also contains an effervescent couple.

DESCRIPTION OF THE INVENTION

The phenylpropanolamine bitartrate or tartrate salts suitable for use in the present invention are now commercially available at a purity acceptable for use in medicinal compounds. Both phenylpropanolamine tartrate and phenylpropanolamine bitartrate are suitable for use in the present invention. The bitartrate salt is the preferred ingredient.

In producing the novel composition of the present invention the various ingredients are appropriately blended together to form a substantially uniform mixture without the necessity of coating or otherwise preventing direct contact between the acetylsalicylic acid and the phenylpropanolamine bitartrate or tartrate salt. The resulting composition can be processed in well known techniques to produce the finished product form as powders, granules, capsules and/or tablets. The relative amounts of acetylsalicylic acid and phenylpropanolamine bitartrate or tartrate salt or mixture thereof are not critical. The relative amounts are governed solely by the medicinal effects desired. It is desirable that a pharmaceutical dose contain about 80 to 650 mg. acetylsalicylic acid and about 5 to 60 mg. phenylpropanolamine bitartrate or tartrate salt or mixture thereof. The overall composition thus contains from about 57 to 99.2 weight percent acetylsalicylic acid and from about 0.8 to 43 weight percent phenylpropanolamine bitartrate or tartrate salt or mixture thereof based upon the total weight of the acetylsalicylic acid and the bitartrate and/or tartrate salts.

The final composition can contain other active medicinal ingredients, excipients, lubricants and effervescent couple components so long as they do not contribute to the instability of the acetylsalicylic acid. The effervescent couple consists of an alkaline material capable of liberating carbon dioxide, such as sodium bicarbonate, sodium carbonate and the like, and an organic acid, such as citric acid, fumaric acid, adipic acid and the like.

The invention will be described in further detail in the following examples.

EXAMPLE 1

A first formulation consisting of a mixture of acetylsalicylic acid, phenylpropanolamine hydrochloride, sodium bicarbonate, citric acid and minor amounts of flavorings was fed to a tabletting machine to form tablets each containing about 325 mg. of acetylsalicylic acid and about 12.5 mg. of phenylpropanolamine hydrochloride. A second formulation consisting of the above ingredients, except that phenylpropanolamine bitartrate was substituted for the phenylpropanolamine hydrochloride, was fed to a tabletting machine to form tablets each containing about 325 mg. of acetylsalicylic acid and about 20 mg. of phenylpropanolamine bitartrate. The formulation and tablets contained about 94 weight percent acetylsalicylic acid and about 6 weight percent phenylpropanolamine bitartrate based upon the total weight of the acetylsalicylic acid and the bitartrate salt. Tablets of each formulation were then stored at 40° C. and samples were removed at intervals, and the salicylic acid per tablet of the samples was measured. The results are shown in the following table.

TABLE 1

| Formulation | Salicylic acid in mg. per tablet storage time at 40° C. | | |
|---|---|---|---|
| | 2 weeks | 1 month | 3 months |
| First | 14.4 | 28.6 | 80.8 |
| Second | 8.6 | 13.0 | 31.2 |

It can be seen from the above data that the use of phenylpropanolamine bitartrate significantly improves the storage stability in contact with acetylsalicylic acid as compared with the hydrochloride salt. The improved stability achieved by use of the phenylpropanolamine bitartrate is commercially acceptable in effervescent systems.

EXAMPLE 2

A formulation consisting of about 10.4 weight percent acetylsalicylic acid, about 0.8 weight percent phenylpropanolamine bitartrate, about 51.3 weight percent sodium bicarbonate, about 36.8 weight percent citric acid, about 0.1 weight percent chlorpheniramine maleate (an antihistamine) and about 0.6 weight percent flavorings was fed to a tabletting machine to form tablets each containing about 324 mg. acetylsalicylic acid and about 24.1 mg. of phenylpropanolamine bitartrate. The formulation and tablets contained about 93 weight percent acetylsalicylic acid and about 7 weight percent phenylpropanolamine bitartrate based upon the total weight of the acetylsalicylic acid and the bitartrate salt. These tablets had acceptable storage stability even with phenylpropanolamine bitartrate in direct contact with the acetylsalicylic acid. They are also suitable for dissolution in water with effervescence for ingestion as a medicinal product suitable for relief of symptoms connected with a cold.

EXAMPLE 3

A first formulation consisting of a mixture of the ingredients of Example 1 was used to form tablets each containing about 650 mg. of acetylsalicylic acid and 23.3 mg. of phenylpropanolamine hydrochloride. A second formulation consisting of a mixture of the ingredients of Example 1 was used to form tablets each containing about 650 mg. of acetylsalicylic acid and 40.9 mg. of phenylpropanolamine bitartrate. Tablets of each formulation were then stored at 40° C. and samples were removed at intervals, and the salicylic acid per tablet was measured. The results are shown in the following table.

TABLE 2

| Formulation | Salicylic acid in mg. per tablet storage time at 40° C. | | |
|---|---|---|---|
| | 2 weeks | 1 month | 3 months |
| First | 13.8 | 28.9 | 87.2 |
| Second | 7.8 | 11.1 | 25.6 |

The improved stability achieved by the use of the phenylpropanolamine bitartrate is commercially acceptable in effervescent systems.

EXAMPLE 4

A formulation consisting of the ingredients of the second formulation of Example 1 was used to form tablets each containing about 81 mg. of acetylsalicylic acid and 5.4 mg. of phenylpropanolamine bitartrate. These tablets were then stored at 40° C. for 3 months. The resulting stability achieved is commercially acceptable in effervescent systems.

While the above examples all employed phenylpropanolamine bitartrate, it should be understood that the tartrate salt or a mixture of the bitartrate and tartrate salts can also be employed in the practice of this invention.

What is claimed is:

1. A stable medicinal composition comprising a substantially uniform mixture of from about 80 to 650 mg. acetylsalicylic acid and from about 5 to 60 mg. of a bitartrate or tartrate salt of phenylpropanolamine or a mixture of such salts in direct contact with the acetylsalicylic acid.

2. A composition according to claim 1 wherein the salt is phenylpropanolamine bitartrate.

3. A composition according to claim 1 also containing an effervescent couple.

4. A composition according to claim 3 wherein the effervescent couple consists of a mixture of sodium bicarbonate and citric acid.

5. A composition according to claim 1 containing about 10.4 weight percent acetylsalicylic acid and about 0.8 weight percent phenylpropanolamine bitartrate, said weight percent based on the total weight of the composition.

6. A composition according to claim 1 containing about 93 weight percent acetylsalicylic acid and about 7 weight percent phenylpropanolamine bitartrate based upon the total weight of the acetylsalicylic acid and the bitartrate salt.

* * * * *